(12) United States Patent
Onishi et al.

(10) Patent No.: US 10,194,784 B2
(45) Date of Patent: Feb. 5, 2019

(54) LINEAR MEMBER DELIVERY DEVICE FOR ENDOSCOPE

(71) Applicant: OLYMPUS CORPORATION, Tokyo (JP)

(72) Inventors: Hideto Onishi, Hachioji (JP); Tomokazu Iwasaki, Hachioji (JP); Young Chung Kim, Singapore (SG)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/619,603

(22) Filed: Jun. 12, 2017

(65) Prior Publication Data

US 2017/0273544 A1    Sep. 28, 2017

Related U.S. Application Data

(63) Continuation of application No. PCT/JP2016/079091, filed on Sep. 30, 2016.

(30) Foreign Application Priority Data

Jan. 28, 2016 (JP) .................................. 2016-014472

(51) Int. Cl.
*A61B 1/00* (2006.01)
*A61B 1/12* (2006.01)

(52) U.S. Cl.
CPC ...... *A61B 1/00071* (2013.01); *A61B 1/00091* (2013.01); *A61B 1/00121* (2013.01); *A61B 1/122* (2013.01); *A61B 1/00112* (2013.01)

(58) Field of Classification Search
CPC ............ A61B 1/00071; A61B 1/00091; A61B 1/00121; A61B 1/00112; A61B 1/00131–1/00137; A61B 90/70; A61B 2090/701; B08B 9/0436
See application file for complete search history.

(56) References Cited

U.S. PATENT DOCUMENTS

| 4,562,830 | A | 1/1986 | Yabe |
| 2012/0285485 | A1 | 11/2012 | Majeed |
| 2015/0045617 | A1 | 2/2015 | Yamada |

FOREIGN PATENT DOCUMENTS

| EP | 0075188 A2 | 3/1983 |
| JP | S58-046933 A | 3/1983 |
| JP | H05-228107 A | 9/1993 |
| JP | 2004-208961 A | 7/2004 |
| JP | 2005-058258 A | 3/2005 |
| JP | 2011-120788 A | 6/2011 |
| KR | 1020160097681 A | 8/2016 |

OTHER PUBLICATIONS

Extended Supplementary European Search Report dated Oct. 18, 2018 in European Patent Application No. 16 86 9375.2.

*Primary Examiner* — Timothy J Neal
(74) *Attorney, Agent, or Firm* — Scully, Scott, Murphy & Presser, P.C.

(57) ABSTRACT

A linear member delivery device for the endoscope includes: a nozzle including an inlet, an outlet, and an insertion path; a fitting portion fitted to an endoscope; a holding portion configured to hold a linear member; and a switching portion configured to connect the fitting portion and the nozzle such that a crossing angle of an opening of the endoscope and a center axis of the nozzle can be switched to a plurality of angles in a state that the fitting portion is fitted to the endoscope.

5 Claims, 12 Drawing Sheets

LINEAR MEMBER DELIVERY DEVICE FOR ENDOSCOPE

CROSS REFERENCE TO RELATED APPLICATION

This application is a continuation application of PCT/JP2016/079091 filed on Sep. 30, 2016 and claims benefit of Japanese Application No. 2016-014472 filed in Japan on Jan. 28, 2016, the entire contents of which are incorporated herein by this reference.

BACKGROUND OF THE INVENTION

1. Field of the Invention

The present invention relates to a linear member delivery device for an endoscope.

2. Description of the Related Art

Conventionally, there is an adapter configured to lead out a cleaning brush configured by a linear member to an endoscope conduit so as to clean the endoscope conduit. For example, an air/water feeding conduit cleaning adapter disclosed in Japanese Patent Application Laid-Open Publication No. H05-228107 is inserted into a cylinder of an endoscope and slid inside the cylinder and thus a lead-out position of a cleaning brush is adjusted to an air feeding conduit or a water feeding conduit opened inside the cylinder and a cleaning brush is led out.

SUMMARY OF THE INVENTION

A linear member delivery device for an endoscope of one aspect of the present invention includes: a nozzle including an inlet configured to introduce a linear member, an outlet configured to lead out the linear member, and an insertion path connecting the inlet and the outlet; a fitting portion fitted to an endoscope such that the outlet faces an opening of the endoscope; a holding portion configured to hold the linear member such that a crossing angle of an axis of the linear member led out from the outlet and a center axis of the nozzle is in a predetermined range; and a switching portion connecting the fitting portion and the nozzle such that a crossing angle of the opening of the endoscope and the center axis of the nozzle can be switched to a plurality of angles in a state that the fitting portion is fitted to the endoscope.

DETAILED DESCRIPTION OF THE PREFERRED EMBODIMENT(S)

Hereinafter, an embodiment of the present invention will be described with reference to the drawings.

(Configuration)

Figure 1:
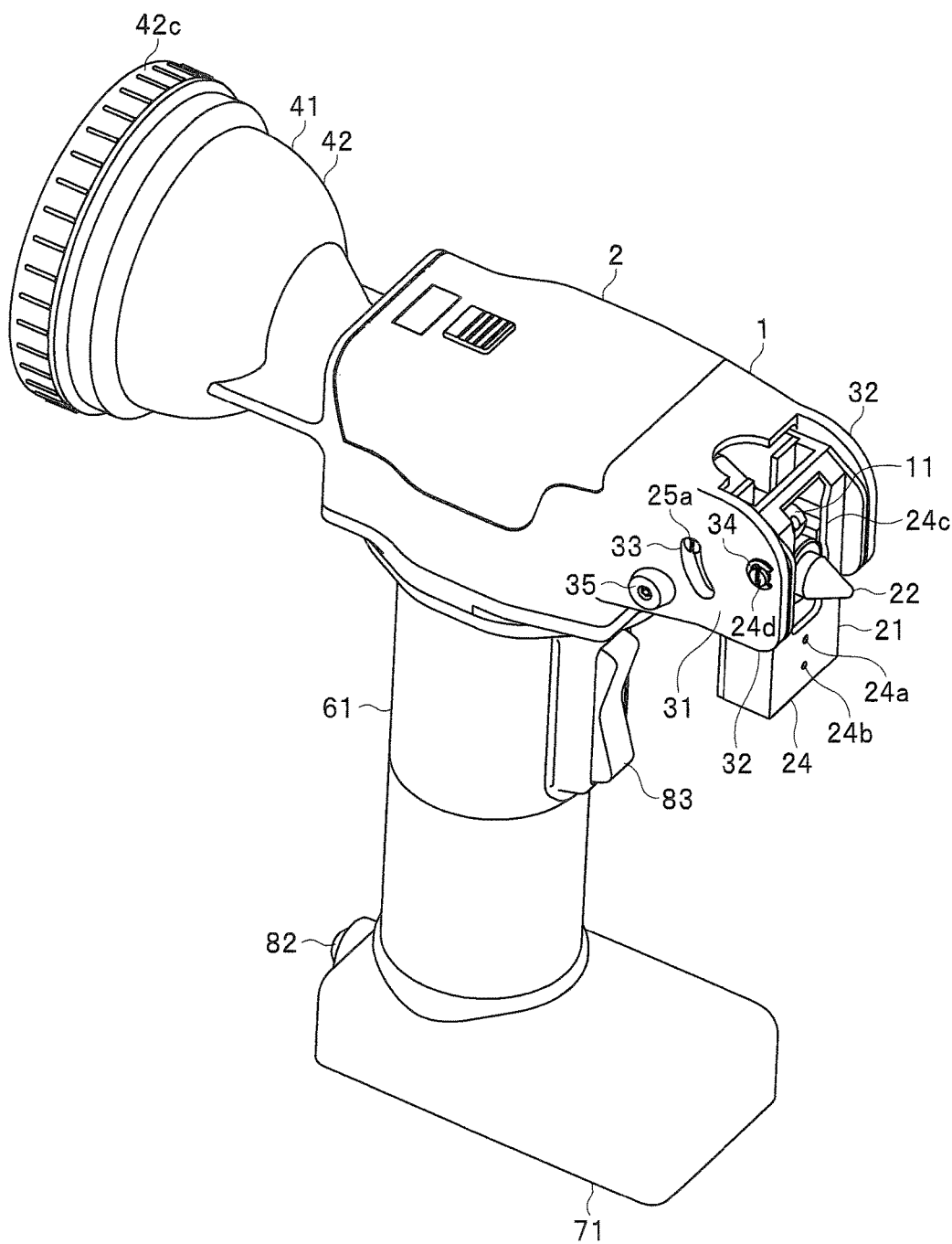
FIG. 1 is a perspective view illustrating an appearance configuration of a linear member delivery device for an endoscope, relating to an embodiment of the present invention.
Figure 2:
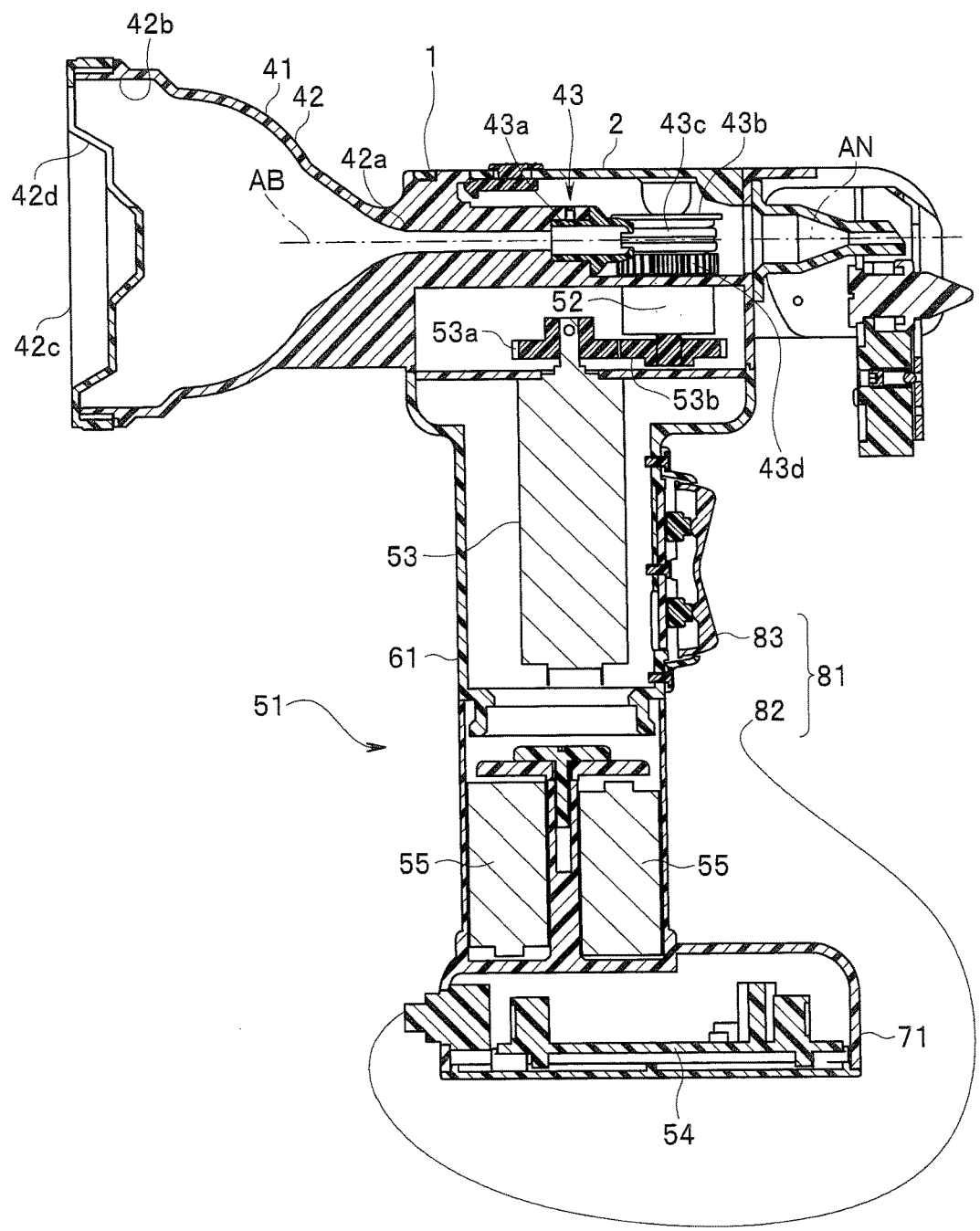
FIG. 2 is a sectional view illustrating a configuration of the linear member delivery device for an endoscope, relating to the embodiment of the present invention.
Figure 3:
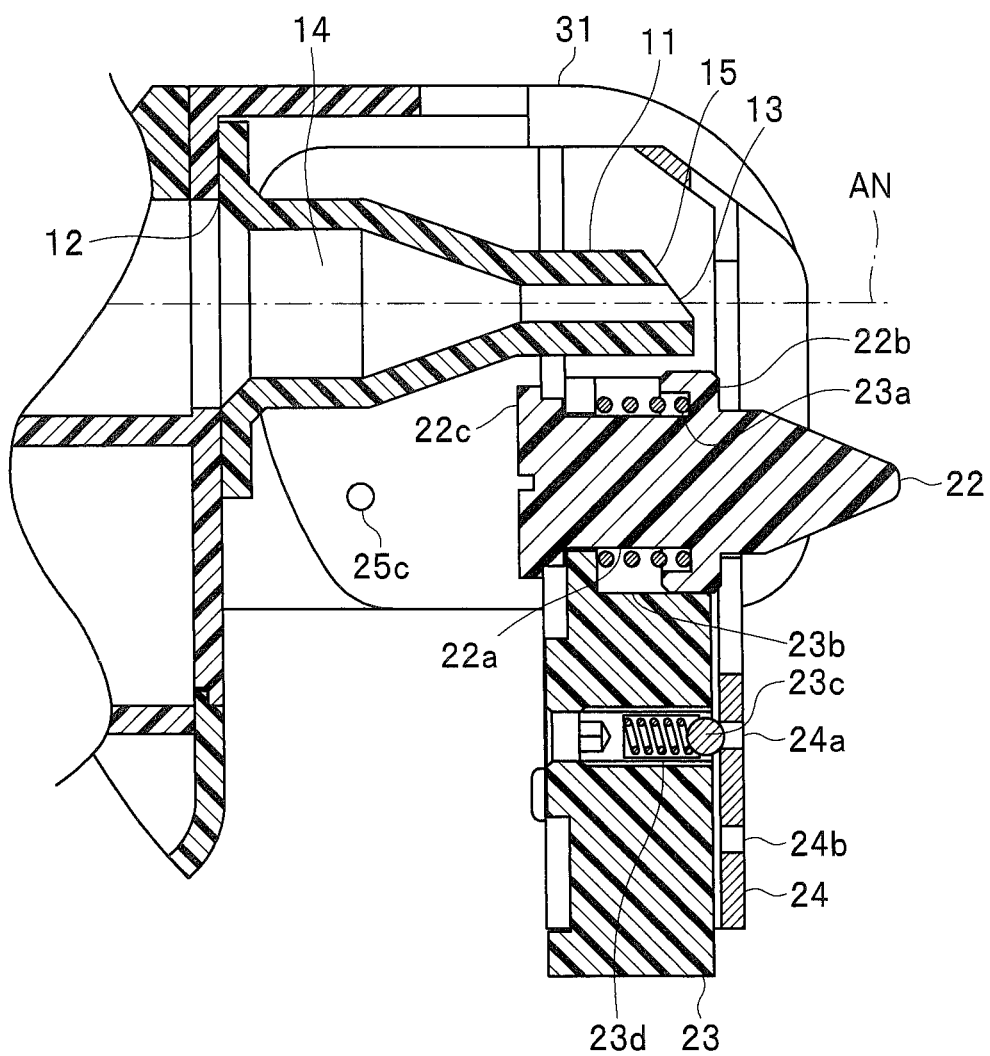
FIG. 3 is an enlarged sectional view illustrating the configuration of a nozzle, a fitting portion and a switching portion of the linear member delivery device for an endoscope, relating to the embodiment of the present invention.
Figure 4:
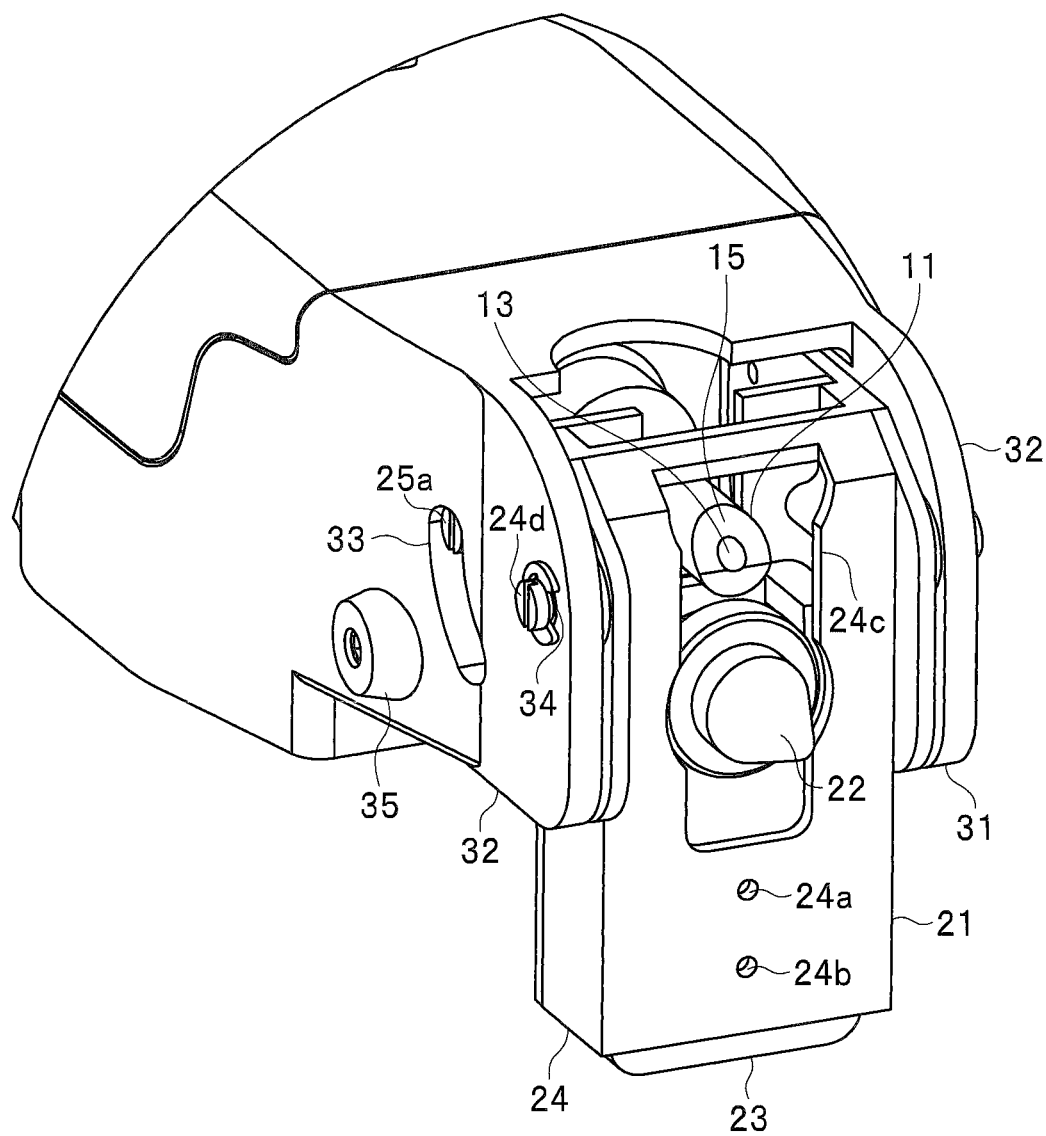
FIG. 4 is an enlarged perspective view illustrating the appearance configuration of the nozzle, the fitting portion and the switching portion of the linear member delivery device for an endoscope, relating to the embodiment of the present invention.
Figure 5:
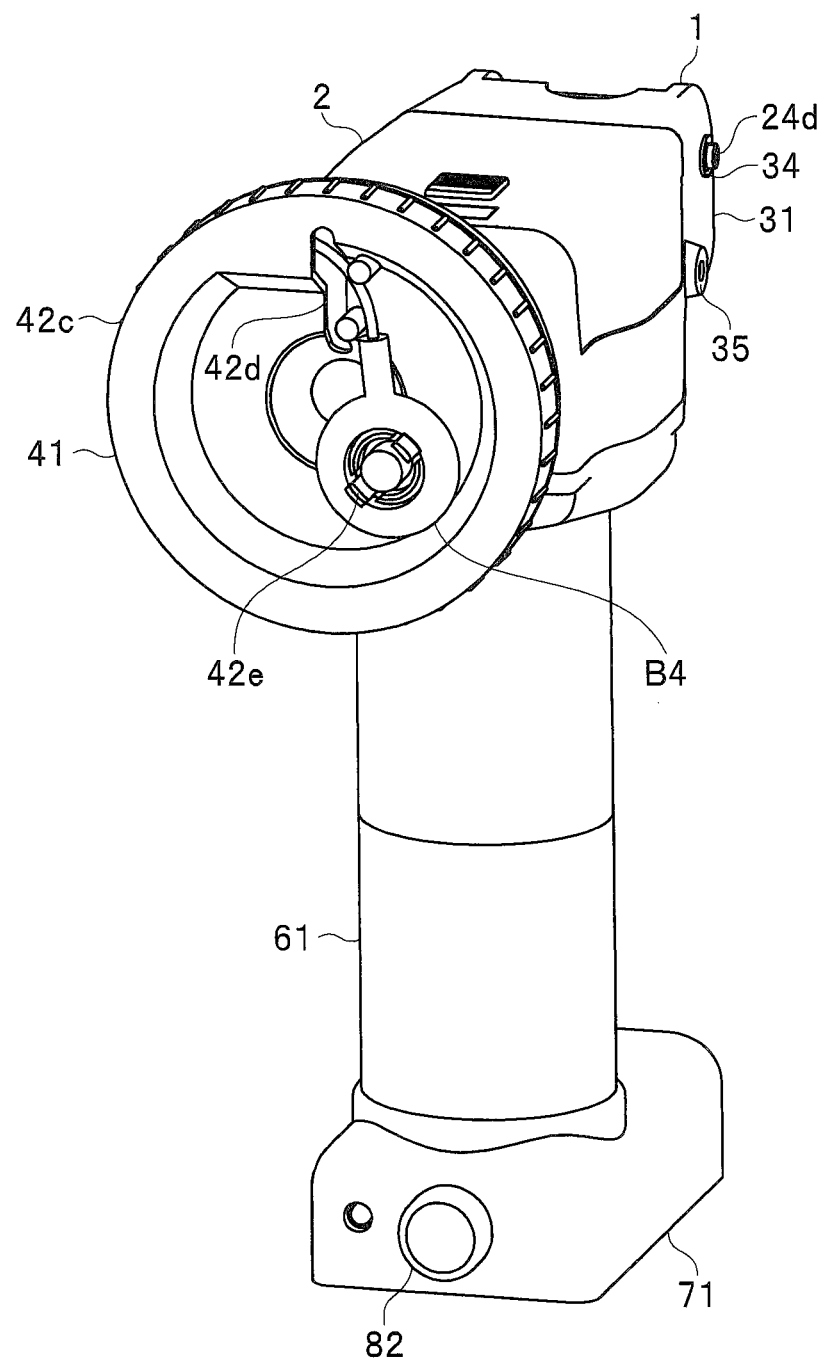
FIG. 5 is a rear perspective view illustrating the appearance configuration of the linear member delivery device for an endoscope, relating to the embodiment of the present invention.
Figure 6:
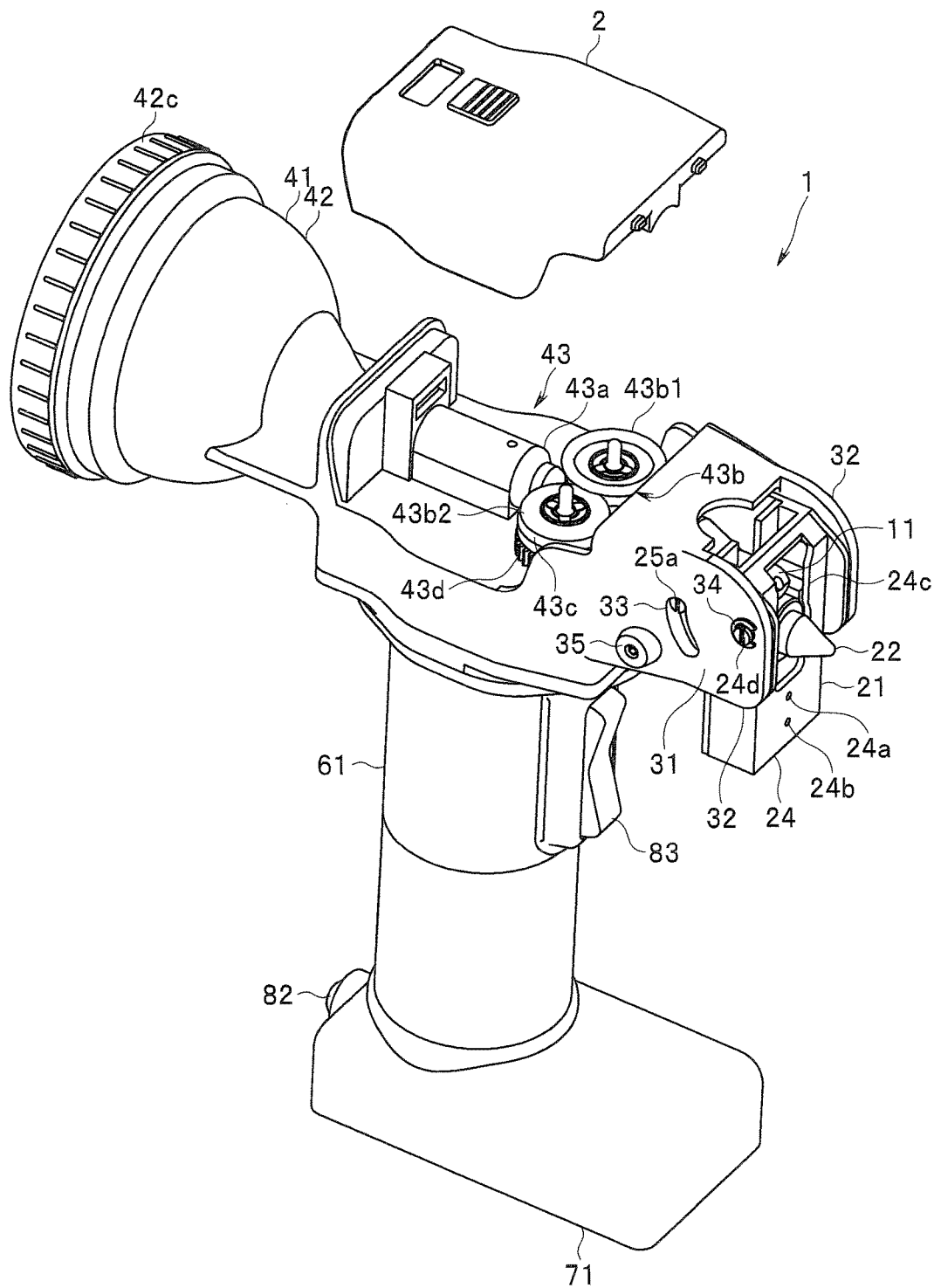
FIG. 6 is a perspective view illustrating the appearance configuration of the linear member delivery device for an endoscope in a state that a cover is detached, relating to the embodiment of the present invention.

FIG. 1 is a perspective view illustrating an appearance configuration of a linear member delivery device 1 for an endoscope, relating to the embodiment of the present invention. FIG. 2 is a sectional view illustrating a configuration of the linear member delivery device 1 for an endoscope, relating to the embodiment of the present invention. FIG. 3 is an enlarged sectional view illustrating the configuration of a nozzle 11, a fitting portion 21 and a switching portion 31 of the linear member delivery device 1 for an endoscope, relating to the embodiment of the present invention. FIG. 4 is an enlarged perspective view illustrating the appearance configuration of the nozzle 11, the fitting portion 21 and the switching portion 31 of the linear member delivery device 1 for an endoscope, relating to the embodiment of the present invention. FIG. 5 is a rear perspective view illustrating the appearance configuration of the linear member delivery device 1 for an endoscope, relating to the embodiment of the present invention. FIG. 6 is a perspective view illustrating the appearance configuration of the linear member delivery device 1 for an endoscope in a state that a cover 2 is detached, relating to the embodiment of the present invention. In FIG. 2, an electrical connection line is omitted.

The linear member delivery device 1 for an endoscope is configured including the nozzle 11, the fitting portion 21, the switching portion 31, a holding portion 41, a drive portion 51, a grasping portion 61, a pedestal portion 71, and an operation portion 81.

The nozzle 11 is configured so as to deliver a cleaning brush B to be described later to a suction cylinder side opening E1 (FIG. 9) of an endoscope E. The nozzle 11 is configured by plastic, for example. The nozzle 11 includes an inlet 12 configured to introduce the cleaning brush B, an outlet 13 configured to lead out the cleaning brush B, and an insertion path 14 configured to connect the inlet 12 and the outlet 13. The insertion path 14 is formed in a cylindrical shape narrowed from the inlet 12 toward the outlet 13. The outlet 13 is formed by inclining at least a portion of an end face to a direction orthogonal to a center axis of the nozzle such that the nozzle 11 does not butt into a pipe sleeve E11 of the suction cylinder side opening E1 when an angle of the nozzle 11 is switched. In the present embodiment, one side 15 of an edge of the outlet 13 is inclined to the direction orthogonal to the center axis of the nozzle and formed.

The fitting portion 21 includes a fitting slit 24c to be described later, and can be fitted to the pipe sleeve E11 in an outward flange shape of the endoscope E. When the fitting portion 21 is fitted to the pipe sleeve E11, the outlet 13 faces the pipe sleeve E11. That is, the fitting portion 21 is fitted to the endoscope E so that the outlet 13 faces the opening of the endoscope E. The fitting portion 21 is configured including a connection guide 22, a slide piece 23, a case body 24, and an extension plate 25.

The connection guide 22 is configured by the plastic, for example. In the connection guide 22, a body portion 22a is formed into a columnar shape and is formed such that a distal end is narrowed, and a shoulder portion 22b and a base portion 22c are formed into a flange shape. In the connection guide 22, a compression spring 23a is externally fitted to the body portion 22a. When the connection guide 22 is attached to a hollow portion 23b provided in the slide piece 23, the compression spring 23a is pressed to the shoulder portion 22b, and the connection guide 22 is energized in a distal end direction of the connection guide 22. For the connection guide 22 energized in the distal end direction, thrusting-out is restricted by the base portion 22c being pressed to the case body 24.

The slide piece 23 is configured by the plastic, for example The slide piece 23 is freely slidably and internally fitted to the case body 24. The slide piece 23 is provided with the hollow portion 23b for attaching the connection guide 22. The slide piece 23 includes a ball plunger 23d incorporating a ball 23c energized in an extrusion direction by the compression spring 23a.

The case body 24 is configured by a metal, for example. The case body 24 is externally fitted to the slide piece 23. The case body 24 includes positioning holes 24a and 24b to which the ball 23c of the ball plunger 23d is to be fitted so that a position in a sliding direction of the slide piece 23 can be switched in two stages. The case body 24 includes the fitting slit 24c so as to slide and fit the pipe sleeve E11 of the endoscope E. The fitting slit 24c is formed such that the nozzle 11 and the connection guide 22 are exposed. The case body 24 includes a turning shaft 24d pivoted to the switching portion 31. The fitting portion 21 is freely turnable around the turning shaft 24d.

The extension plate 25 is extended respectively from both side portions of the case body 24 so as to be connected to the switching portion 31. Each extension plate 25 is provided with a pin 25a loosely fitted to a bent long hole 33 of the switching portion 31 so as to restrict a turning range of the fitting portion 21. Each extension plate 25 includes positioning holes 25b (FIG. 12) and 25c to which a ball not shown in the figure of a ball plunger 35 (to be described later) is to be fitted so that the position in a turning direction of the fitting portion 21 can be switched in two stages.

The switching portion 31 connects the fitting portion 21 and the nozzle 11 such that a crossing angle of the suction cylinder side opening E1 and a center axis AN of the nozzle 11 is switched to a plurality of angles in a plurality of stages in the state that the fitting portion 21 is fitted to the endoscope E.

The switching portion 31 is configured by the plastic, for example. The switching portion 31 includes two support plates 32 arranged facing each other so as to hold the fitting portion 21 with each other. Each of the two support plates 32 includes a bearing hole 34 configured to pivot the turning shaft 24d of the fitting portion 21, the bent long hole 33 configured to restrict the turning range of the fitting portion 21, and the ball plunger 35 capable of switching a turning angle of the fitting portion 21 in two stages. Thus, the switching portion 31 can pivot the fitting portion 21 and switch the crossing angle of the suction cylinder side opening E1 and the center axis AN of the nozzle 11 in two stages.

The holding portion 41 is configured to hold the cleaning brush B such that the crossing angle of an axis AB of the cleaning brush led out from the outlet 13 of the nozzle 11 (in FIG. 2, the cleaning brush is omitted and only the axis is illustrated) and the center axis AN of the nozzle is in a predetermined range. The holding portion 41 is configured including a housing portion 42 and a connection portion 43.

The housing portion 42 is configured to house the cleaning brush B in a wound state. The housing portion 42 is configured by the plastic, for example. The housing portion 42 is in a bottomed cylindrical shape, and includes a cylindrical sidewall 42b narrowed toward an opening 42a and a bottom portion 42c (FIG. 5) configured by an attachable and detachable cap.

To the opening 42a, a guide 43a (to be described later) is attached.

The bottom portion 42c includes a ring draw-out hole 42d and a ring hook 42e. A ring B4 at a rear end of the cleaning brush B is drawn out from the ring draw-out hole 42d of the bottom portion 42c and hooked to the ring hook 42e. Note that the housing portion 42 may not include the ring draw-out hole 42d and the ring hook 42e.

The connection portion 43 is configured to connect the housing portion 42 and the inlet 12 of the nozzle 11. The connection portion 43 is configured including the guide 43a and a roller 43b which is a transfer portion. As illustrated in FIG. 6, the attachable and detachable cover 2 is provided so as to cover an upper part of the connection portion 43, and by detaching the cover 2, the connection portion 43 can be exposed.

The guide 43a is provided between the roller 43b and the opening 42a of the housing portion 42, and is formed so as to be narrowed from the opening 42a to the roller 43b, in other words, to be widened from the roller 43b to the opening 42a. The guide 43a can house a brush B2 of the cleaning brush B, and guides the cleaning brush B sent out to the roller 43b.

The roller 43b is arranged in the connection portion 43, and is configured to transfer the cleaning brush B at least from the inlet 12 toward the outlet 13. In FIG. 2 and FIG. 6, the roller 43b is arranged in the connection portion 43. Note that the roller 43b may be arranged inside the insertion path 14 of the nozzle 11 or the housing portion 42.

The roller 43b is configured by a drive roller 43b1 and a driven roller 43b2 arranged facing each other. Each of the drive roller 43b1 and the driven roller 43b2 includes an anti-skid rubber ring 43c on an outer periphery. The drive roller 43b1 is connected to a drive shaft 52 of the drive portion 51, and is rotationally driven by the drive portion 51.

Each of the drive roller 43b1 and the driven roller 43b2 includes two gears 43d that engage with each other at a proximal end. The drive roller 43b1 transmits rotating force to the driven roller 43b2 by the two gears 43d, and rotates the driven roller 43b2 in a direction opposite to the drive roller 43b1. The drive roller 43b1 and the driven roller 43b2 can transfer the cleaning brush B in a direction from the inlet 12 toward the outlet 13 or in a direction from the outlet 13 toward the inlet 12 by being rotationally driven.

Figure 7:
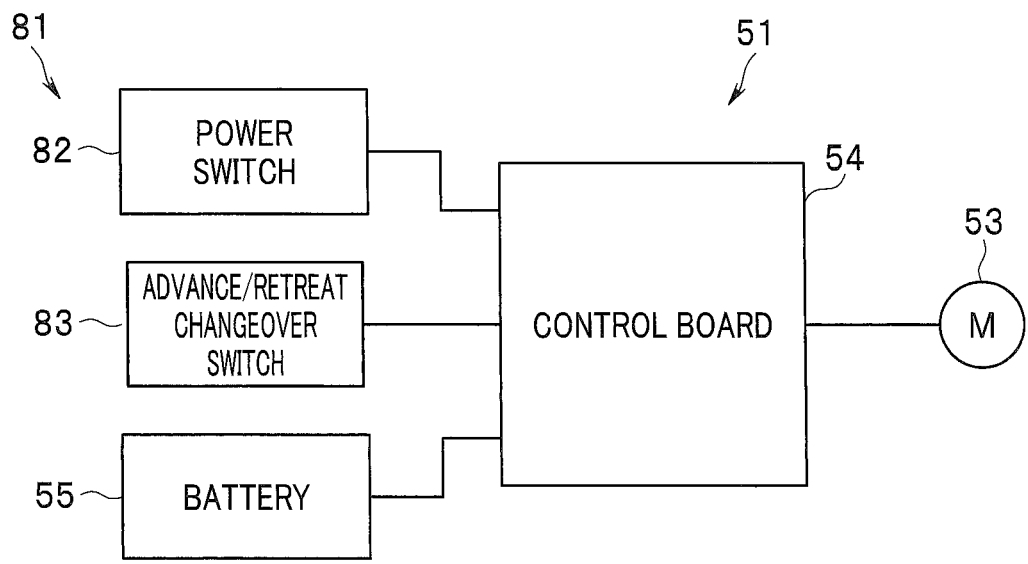
FIG. 7 is an explanatory diagram describing the configuration of a drive portion and an operation portion of the linear member delivery device for an endoscope, relating to the embodiment of the present invention.

FIG. 7 is an explanatory diagram describing the configuration of the drive portion 51 and the operation portion 81 of the linear member delivery device 1 for an endoscope, relating to the embodiment of the present invention.

As illustrated in FIG. 7, the drive portion 51 is configured including a motor 53, a control board 54, and a battery 55.

The motor 53 transmits the rotating force to a gear 53a connected to a motor shaft, a gear 53b that engages with the gear 53a, the drive shaft 52 connected to the gear 53b, and the drive roller 43b1 connected to the drive shaft 52. The motor 53 is provided inside the grasping portion 61. The motor 53 is connected to the control board 54. The motor 53 rotationally drives the roller 43b under control of the control board 54.

The control board 54 is configured including a circuit configured to control rotation of the motor 53. The control board 54 is provided inside the pedestal portion 71. The control board 54 is connected to the battery 55 and the operation portion 81. The control board 54 supplies electric power of the battery 55 to the motor 53 and rotates the motor 53, according to instruction input inputted through the operation portion 81.

The battery 55 supplies the electric power to the motor 53 under the control of the control board 54.

The operation portion 81 is configured including a power switch 82 and an advance/retreat switch 83. The operation portion 81 is connected to the control board 54. When an instruction is inputted to the operation portion 81, the instruction input is outputted to the control board 54.

The power switch 82 is configured to input the instruction of ON/OFF changeover of a power source.

The advance/retreat switch 83 is configured to input the instruction of advance or retreat of the cleaning brush B, that is, delivery or draw-in of the cleaning brush B.

Next, the cleaning brush B housed in the linear member delivery device 1 for an endoscope and delivered from the linear member delivery device 1 for an endoscope will be described.

Figure 8:
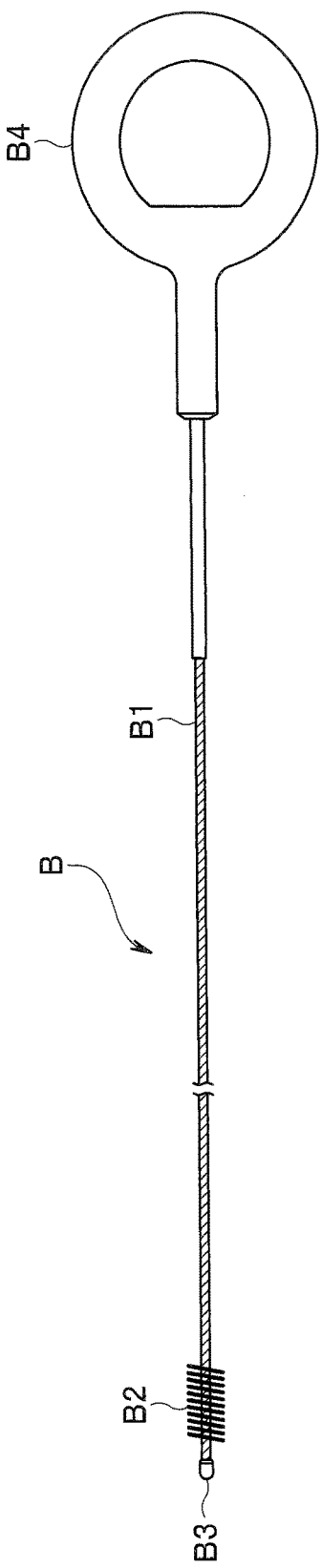
FIG. 8 is a diagram illustrating an example of a cleaning brush of the linear member delivery device for an endoscope, relating to the embodiment of the present invention.

FIG. 8 is a diagram illustrating an example of the cleaning brush B of the linear member delivery device 1 for an endoscope, relating to the embodiment of the present invention.

The cleaning brush B is configured including a shaft B1, the brush B2, a distal end chip B3, and the ring B4.

The shaft B1 is formed in a thin and long shape by tightly winding a thin metal wire in a coil shape. The shaft B1 has a sufficient length enough to be inserted into a conduit of the endoscope E and clean the conduit of the endoscope E by the brush B2 provided on a distal end. The shaft B1 is configured having restoration force to return to a straight shape.

The brush B2 is provided on the distal end of the shaft B1. The brush B2 is formed in a size that can pass through while rubbing the conduit of the endoscope E. Note that, instead of the brush B2, other members such as sponge or rubber that can pass through while rubbing the conduit of the endoscope E may be provided.

The distal end chip B3 is provided on the distal end of the shaft B1 so that the roller 43b easily draws in the cleaning brush B.

The ring B4 is provided on a rear end of the shaft B1, and can be hooked to the ring hook 42e of the holding portion 41. Note that the ring B4 may not be provided.

When the cleaning brush B is drawn into the housing portion 42 by the rotation of the roller 43b, the shaft B1 is successively bent along the sidewall 42b of the housing portion 42, and is housed in the housing portion 42 in the wound state.

The cleaning brush B housed in the housing portion 42 in the wound state causes send-out force for sending out the cleaning brush B from the opening 42a of the housing portion 42 to be generated by the restoration force to return to the straight shape. By the send-out force of the cleaning brush B, the distal end chip B3 is pressed to the roller 43b, and the brush B2 is arranged inside the guide 43a.

(Operation)

Subsequently, the operation of the linear member delivery device 1 for an endoscope will be described.

Figure 9:
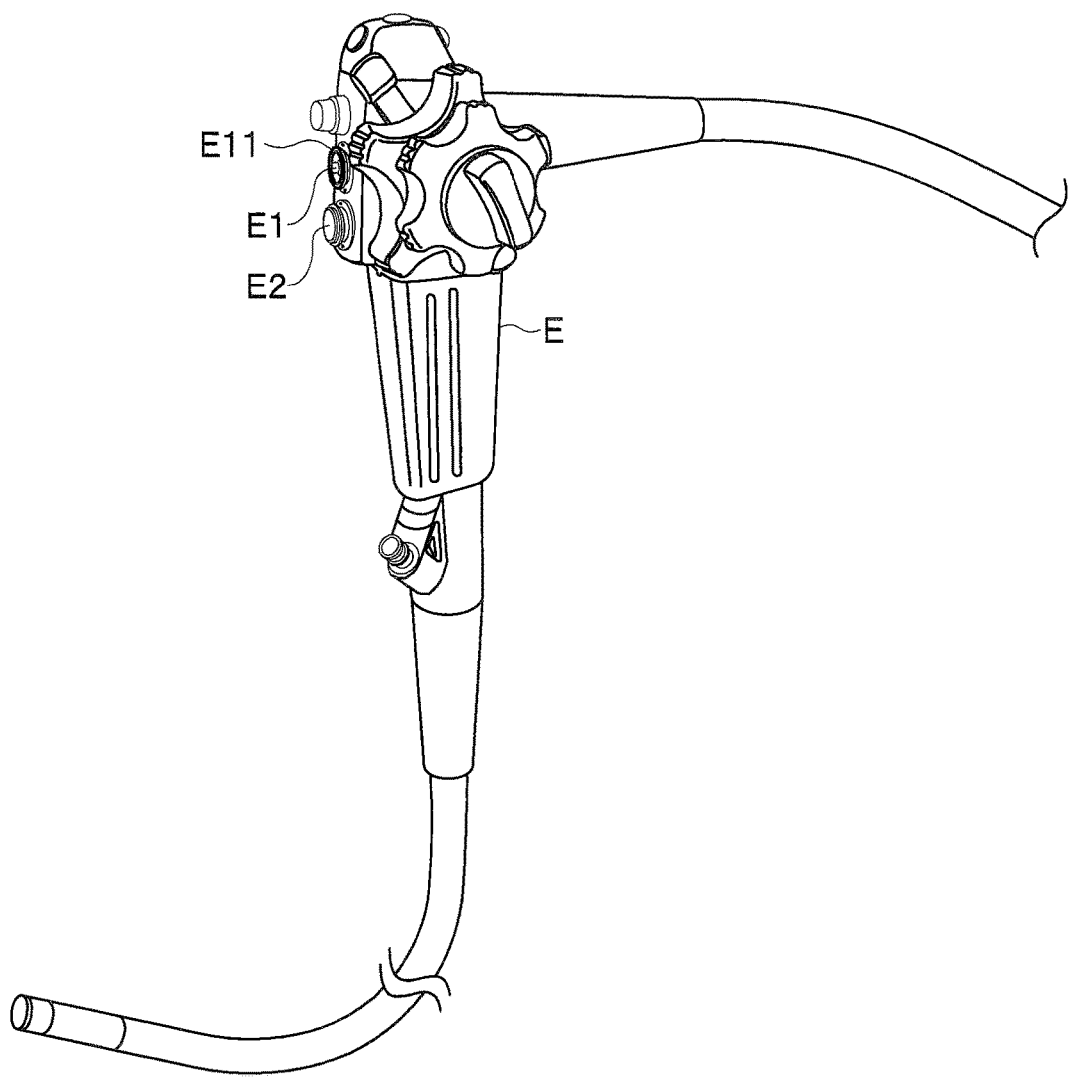
FIG. 9 is a diagram illustrating an example of the appearance configuration of the endoscope to which the linear member delivery device for an endoscope is attached, relating to the embodiment of the present invention.
Figure 10:
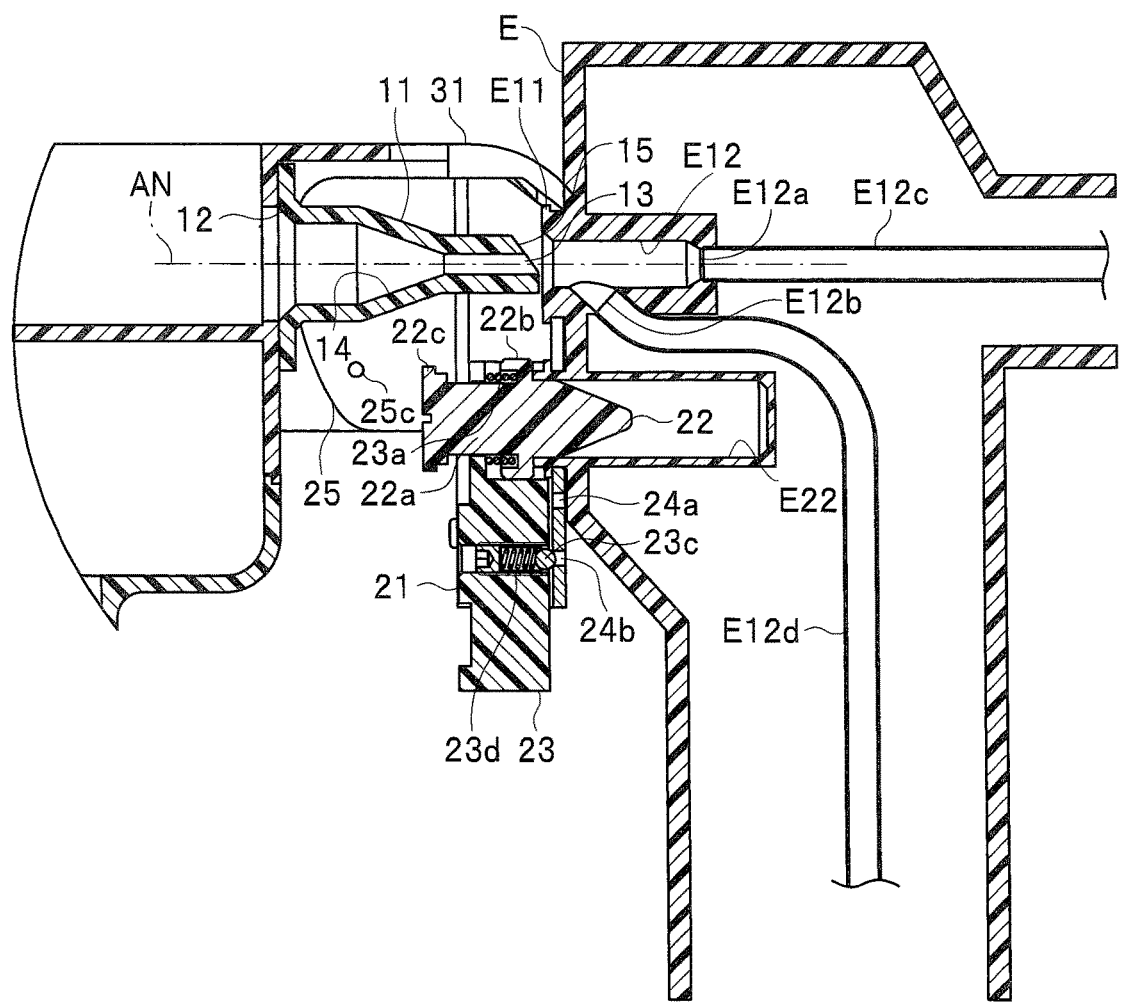
FIG. 10 is an explanatory diagram describing a state that the nozzle of the linear member delivery device for an endoscope is turned to a universal cord side conduit, relating to the embodiment of the present invention.
Figure 11:
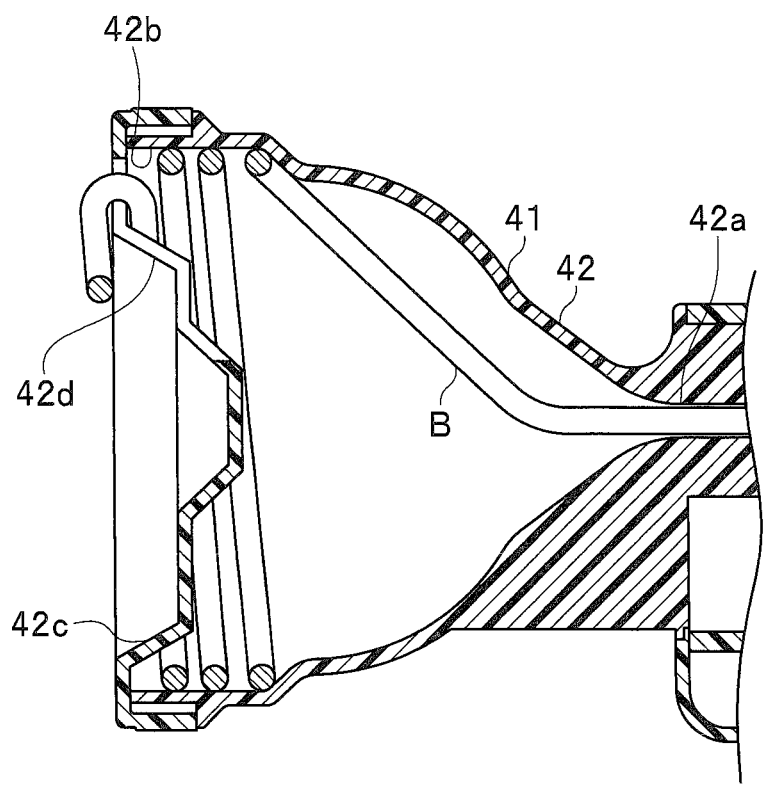
FIG. 11 is an explanatory diagram describing a state that the cleaning brush of the linear member delivery device for an endoscope is housed in a housing portion, relating to the embodiment of the present invention.
Figure 12:
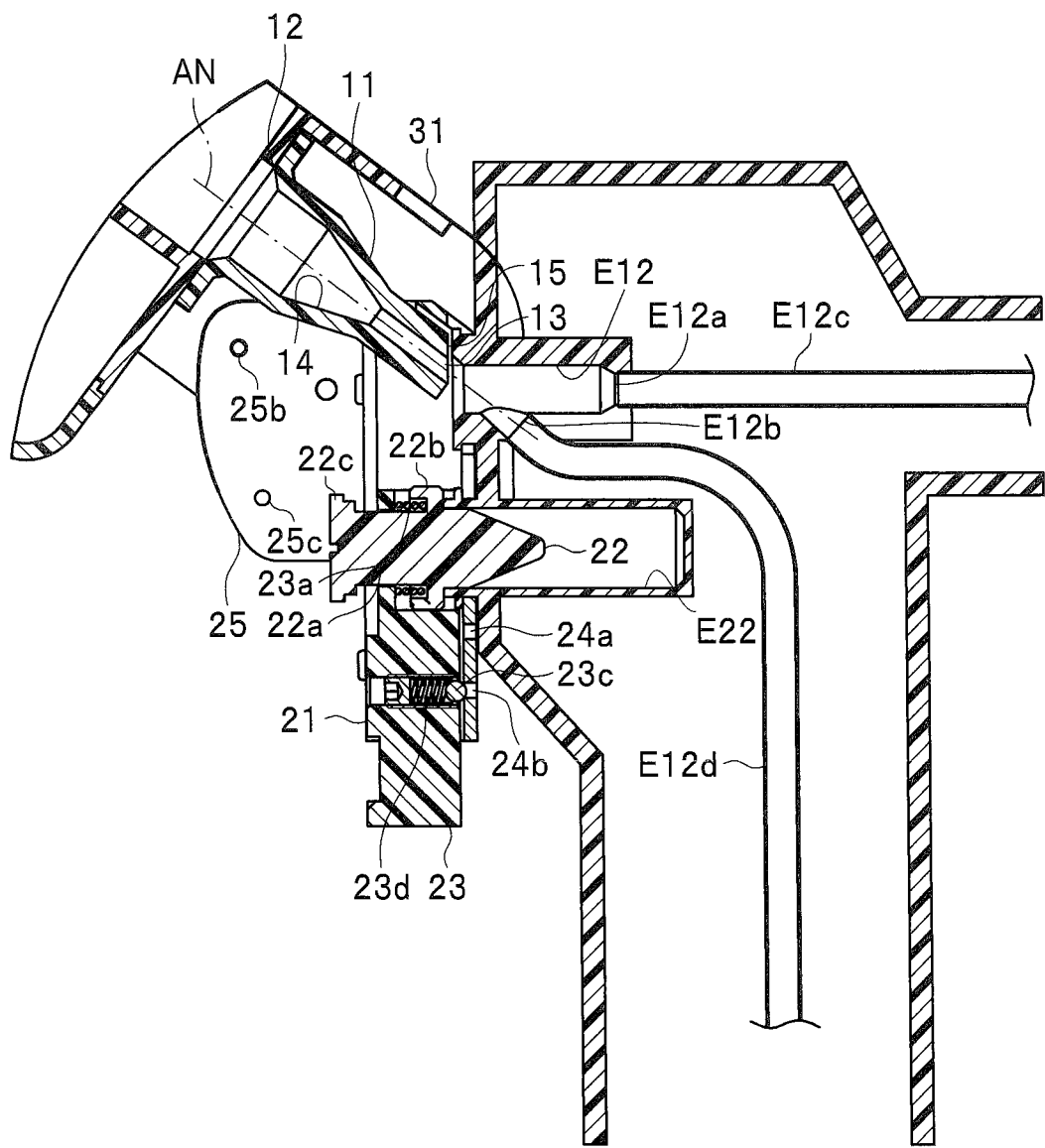
FIG. 12 is an explanatory diagram describing a state that the nozzle of the linear member delivery device for an endoscope is turned to an insertion portion side conduit, relating to the embodiment of the present invention.

FIG. 9 is a diagram illustrating an example of the appearance configuration of the endoscope E to which the linear member delivery device 1 for an endoscope is attached, relating to the embodiment of the present invention. FIG. 10 is an explanatory diagram describing a state that the nozzle 11 of the linear member delivery device 1 for an endoscope is turned to a universal cord side conduit E12c, relating to the embodiment of the present invention. FIG. 11 is an explanatory diagram describing a state that the cleaning brush B of the linear member delivery device 1 for an endoscope is housed in the housing portion 42, relating to the embodiment of the present invention. FIG. 12 is an explanatory diagram describing a state that the nozzle 11 of the linear member delivery device 1 for an endoscope is turned to an insertion portion side conduit E12d, relating to the embodiment of the present invention.

As illustrated in FIG. 9, the endoscope E is configured including the suction cylinder side opening E1 and an air/water feeding cylinder side opening E2. A suction cylinder E12 is formed into the cylindrical shape, and includes a universal cord side opening E12a and an insertion portion side opening E12b. An air/water feeding cylinder E22 is formed into the cylindrical shape.

As illustrated in FIG. 10, when the connection guide 22 is inserted into the air/water feeding cylinder E22, the air/water feeding cylinder side opening E2 is pressed to the shoulder portion 22b of the connection guide 22. Then, the shoulder portion 22b of the connection guide 22 is pushed down against energizing force of the compression spring 23a, and the pipe sleeve E11 of the suction cylinder E12 enters an inner side of the case body 24 of the fitting portion 21 from the fitting slit 24c. Next, when the endoscope E is slid in a direction from the suction cylinder E12 to the air/water feeding cylinder E22, the slide piece 23 is slid together with the connection guide 22 inserted into the endoscope E, and the ball 23c of the ball plunger 23d is fitted to the positioning hole 24b of the case body 24 and positioned. Thus, the pipe sleeve E11 of the suction cylinder E12 is slid and fitted to the case body 24, and the nozzle 11 is turned to the universal cord side opening E12a inside the suction cylinder E12.

When the power source is turned to an ON state by the power switch 82 and the instruction to deliver the cleaning brush B is inputted by the advance/retreat switch 83, the instruction input is inputted to the control board 54, and the control board 54 makes a current flow to the motor 53, rotates the motor 53, and rotates the roller 43b. Then, the roller 43b draws in the distal end chip B3 of the cleaning brush B pressed to the roller 43b, transfers the shaft B1 of the cleaning brush B to the nozzle 11, and delivers the cleaning brush B from the nozzle 11 to the suction cylinder E12. The delivered cleaning brush B enters the universal cord side conduit E12c from the universal cord side opening E12a, and rubs and cleans an inside of the universal cord side conduit E12c.

When the instruction to draw in the cleaning brush B is inputted by the advance/retreat switch 83, the control board 54 rotates the motor 53 in the direction opposite to a delivery direction. When the motor 53 is rotated, the roller 43b draws in the shaft B1 of the cleaning brush B. As illustrated in FIG. 11, the shaft B1 of the drawn-in cleaning brush B is bent along the sidewall 42b of the housing portion 42, and is successively housed in the housing portion 42 in the wound state. When the distal end chip B3 at the distal end of the cleaning brush B passes through the roller 43b, the draw-in of the cleaning brush B is completed.

As illustrated in FIG. 12, when the fitting portion 21 is turned around the turning shaft 24d, the ball not shown in the figure of the ball plunger 35 of the switching portion 31 is fitted to the positioning hole 25b of the extension plate 25 of the fitting portion 21, and the nozzle 11 is turned to the insertion portion side opening E12b inside the suction cylinder E12. When the instruction for delivering the cleaning brush B is inputted by the advance/retreat switch 83, the cleaning brush B enters the insertion portion side conduit E12d from the insertion portion side opening E12b, and cleans the inside of the insertion portion side conduit E12d.

According to the embodiment, to the universal cord side conduit E12c and the insertion portion side conduit E12d opened inside the suction cylinder E12, the cleaning brush B can be easily delivered without damaging a cylinder inner wall.

According to the embodiment, the cleaning brush B passes through the inside of the suction cylinder E12 so that the inside of the suction cylinder E12 can be also cleaned together with cleaning of the universal cord side conduit E12c or the insertion portion side conduit E12d.

Note that, in the embodiment, the example is described in which the linear member delivery device 1 for an endoscope delivers the cleaning brush B from an outer side of the suction cylinder side opening E1 of the endoscope E, however, the linear member delivery device 1 for an endoscope may be configured to deliver the linear member from the outer side of the other opening of the endoscope.

Note that, in the embodiment, the example is described in which the linear member is the cleaning brush B, however, the linear member is not limited to the cleaning brush B, and may be a treatment instrument such as a cytodiagnosis brush, grasping forceps or a cannula.

The present invention is not limited to the above-described embodiment and can be variously changed and modified or the like without changing a subject matter of the present invention.

According to the present invention, a linear member delivery device for an endoscope capable of easily delivering a linear member to a plurality of conduits opened inside a cylinder without damaging a cylinder inner wall can be provided.

What is claimed is:

1. A linear member delivery device for an endoscope comprising:
    a nozzle including an inlet configured to introduce a linear member, an outlet configured to lead out the linear member, and an insertion path connecting the inlet and the outlet;
    a fitting portion configured to be fitted to an endoscope such that the outlet faces an opening of the endoscope;
    a holding portion configured to hold the linear member such that a crossing angle of an axis of the linear member led out from the outlet and a center axis of the nozzle is in a predetermined range; and
    a switching portion connecting the fitting portion and the nozzle such that a crossing angle of the opening of the endoscope and the center axis of the nozzle can be switched to a plurality of angles in a state that the fitting portion is fitted to the endoscope.

2. The linear member delivery device for the endoscope according to claim 1,
    wherein the switching portion switches the crossing angle of the opening of the endoscope and the center axis of the nozzle in a plurality of stages, and
    the outlet is formed by inclining at least a portion of an end face of the nozzle to a direction orthogonal to the center axis of the nozzle.

3. The linear member delivery device for the endoscope according to claim 1,
    wherein the holding portion includes:
    a housing portion where the linear member is housed in a wound state; and
    a connection portion configured to connect the housing portion and the inlet.

4. The linear member delivery device for the endoscope according to claim 1, comprising a transfer portion arranged in the insertion path or the holding portion and configured to transfer the linear member at least from the inlet toward the outlet.

5. The linear member delivery device for the endoscope according to claim 1, wherein the fitting portion is configured to be fitted to a suction cylinder of the endoscope.

* * * * *